(12) United States Patent
Mirza

(10) Patent No.: US 8,512,772 B1
(45) Date of Patent: Aug. 20, 2013

(54) DIETARY SUPPLEMENT FOR PROMOTION OF HAIR PIGMENT RESTORATION

(76) Inventor: Asma Mirza, Piscataway, NJ (US)

( * ) Notice: Subject to any disclaimer, the term of this patent is extended or adjusted under 35 U.S.C. 154(b) by 182 days.

(21) Appl. No.: 12/807,083

(22) Filed: Aug. 27, 2010

(51) Int. Cl.
*A61K 36/55* (2006.01)
(52) U.S. Cl.
USPC .......................................................... 424/768
(58) Field of Classification Search
None
See application file for complete search history.

(56) References Cited

FOREIGN PATENT DOCUMENTS

| CN | 1803166 A | * | 7/2006 |
| JP | 2005247736 A | * | 9/2005 |

OTHER PUBLICATIONS

O'Donnel, K. "A Bean Burger Worth Biting Into". Internet Posting Date: May 16, 2008 [Retrieved from the Internet on: Aug. 30, 2012]. Retrieved from: <URL: http://blog.washingtonpost.com/mighty-appetite/2008/05/a_bean_burger_worth_biting_int.html>.*

"theveggiequeen". Web Posting Date: Apr. 20, 2008 [Retrieved from the Internet on: Aug. 30, 2012]. Retrieved from: <URL: http://voices.washingtonpost.com/mighty-appetite/2009/04/meatless_monday_another_top-sh.html>.*

Alden, L. "The Cook's Thesaurus: Global Spices". Internet Archive date: Aug. 24, 2000 [Retrieved from the Internet on: Aug. 30, 2012]. Retrieved from: <URL: http://web.archive.org/web/20000824122142/http://www.foodsubs.com/SpiceUniv.html>.*

Tanzilo, B. "OnMilwakee.com: Walnut burger is a Wisconsin invention". Internet Posting Date: Sep. 7, 2008. [Retrieved from the Internet on: Aug. 30, 2012]. Retrieved from: <URL: http://onmilwaukee.com/articles/print/wanutburger.html>.*

(U1) "Curing Grey Hair Naturally!". Internet Posting Date: Jun. 4, 2008. [Retrieved from the Internet on: Aug. 30, 2012]. Retrieved from: <URL: http://www.articlesbase.com/hair-loss-articles/curing-grey-hair-naturally-438444.html>.*

* cited by examiner

*Primary Examiner* — Amy L Clark
(74) *Attorney, Agent, or Firm* — Lawrence G. Fridman

(57) ABSTRACT

A dietary supplement which is useful for human hair pigment augmentation is provided. The dietary supplement contains black beans, black seeds, walnuts and flaxseeds, which are arranged in substantially equal amounts. This human hair pigment augmentation is achieved naturally without the use of dyes, colorants, or the like.

9 Claims, No Drawings

DIETARY SUPPLEMENT FOR PROMOTION OF HAIR PIGMENT RESTORATION

FIELD OF THE INVENTION

The present invention relates in general to dietary/food supplements, and in particular to dietary/food supplement for maintaining hair pigment levels, promoting darkening of hair color and hair pigment restoration.

BACKGROUND OF THE INVENTION

Human hair is the keratin-containing threadlike outgrowths extending from hair follicles in the skin. In humans, hair generally serves protective, sensory, and sexual attractiveness functions. Without being bound by any particular theory, it is believed that a mature hair shaft is composed of three, and sometimes four, basic structures. The cuticle is the thick outer protective covering consisting of flat overlapping scale-like layers. The cortex is located inside, and is surrounded by, the cuticle. The cortex contains fibrous proteins which are aligned along the length of the hair axis. Thicker hairs often contain one or more porous regions—the medulla—located near or at the center of the hair shaft. The fourth basic component is the intercellular cement which glues or binds the cells together and provides the main pathway for diffusion into the hair fibers. Melanocytes which produce melanin, the pigment responsible for hair color, are generally contained in the cortex and the base of the bulb of the hair shaft. Essential nutrients and oxygen are carried to the growing hair through capillaries around the base of the bulb.

Hair color is the pigmentation of hair follicles due to two types of melanin, eumelanin and pheomelanin. Generally, if more melanin is present, the color of the hair is darker; if less melanin is present, the hair is lighter. Levels of melanin can vary over time causing a person's hair color to change, and it is possible to have hair follicles of more than one color. Black hair is the darkest and most common of all human hair colors globally. It is a dominant genetic trait, and it is found in people of all backgrounds and ethnicities. It has large amounts of eumelanin and is less dense than other hair colors. Brown hair is characterized by higher levels of the dark pigment eumelanin and lower levels of the pale pigment pheomelanin. Red hair (also referred to as titian or ginger hair) varies from a deep orange-red through burnt orange to bright copper. It is characterized by high levels of the reddish pigment pheomelanin and relatively low levels of the dark pigment eumelanin. Grey or white hair is not actually a true grey or white pigment. In fact, it is clear due to lack of pigmentation and melanin. The clear hairs are seen as grey or white because of the way light hits it.

Grey hair is often considered to be inevitable part of life and the aging process. Graying of hair generally results from a gradual replacement of pigmented hair by unpigmented hair as the melanocytes shut down pigment production as one gets older. This graying process often starts at around age forty (although it can begin much earlier or later) with the onset and rate of graying apparently controlled mainly by genetics. By some estimates, approximately 50 percent of all women will be at least partially grey by the age of fifty. In most cases, the graying process has generally been considered irreversible; once the hair follicle starts to produce grey hair, it is not likely to change back. Thus, for most individuals with graying or already-turned grey hair the options are limited: acceptance of the situation or masking with colorants, bleaches, dyes, highlights, head coverings, or wigs. However, once coloring techniques are used they must be repeated (or at least touched up) on a regular basis to maintain the color and avoid undesirable grey roots.

A substantial number of hair treatment cosmetic preparations are unsatisfactory since they contain chemical compounds that are not needed to repair the hair. Such unneeded chemical compounds may cause additional damage to the hair or coat the hair in a manner that adversely impacts the appearance of the hair. Other treatments target specific types of damage and may require combination with other cosmetic treatments to repair all of the damage to the hair. Interactions between the various cosmetic treatments may create additional difficulties. Persons having sensitive skin may experience adverse reactions to the chemicals present within these cosmetic treatments.

Many of these remedies or therapies whether they be found in the scientific, patent or popular literature have met with varying degrees of success; ranging from outright failure for the most part to drugs such as Rogaine® (minoxidil) which has been approved by the Food and Drug Administration for promoting hair growth. Rogaine has met with a limited degree of success in promoting hair growth and has caused at least some of its users to suffer from certain adverse reactions to their scalps. In addition, it must be used on a continuing basis, there can be no cessation in its use, and it is an expensive medicine.

The following publications are being incorporated in their entireties by reference:
Ansel's Pharmaceutical Dosage Forms and Drug Delivery Systems Loyd V Allen (Editor), Nicholas G. Popovich (Editor), Howard C. Ansel (Editor) Lippinott Williams & Wilkins; Ninth Edition (Jan. 1, 2010), and
Remington: The Science and Practice of Pharmacy (Remington the Science and Practice of Pharmacy) Lippincott Williams & Wilkins; Twenty first Edition (May 1, 2005)

Thus, it has been long felt and unsolved need, therefore, to provide alternatives for combating grey hair, especially ones which will increase and promote the overall healthiness of the hair. There is also a need to provide a method by which, grey hair development can be significantly delayed and prevented. It would also be desirable to provide a method by which, at least in some cases, already-turned grey hair can be restored to its original natural color.

Accordingly, it is an object of the present invention to provide a dietary/food supplement which contains naturally occurring ingredients which are, in combination, effective for promotion of hair pigment restoration.

SUMMARY OF THE INVENTION

Accordingly, it is an object of the present invention to provide a dietary/food supplement which contains naturally occurring ingredients which are, in combination, effective for promotion of hair pigment restoration. The dietary supplement and methods of the present invention, provide such benefits and advantages.

The present invention provides a dietary/food supplement containing a composition of the ingredients the inventor has found to promote the darkening and regrowth of human hair.

In a one embodiment, the ingredients of the dietary supplement, includes black beans, black seeds, walnuts and flaxseeds. The ingredients are usually administered in generally equal amounts; relative to each other, but excluding ancillary dosage form elements such as excipients lubricants, capsules, effervescent and coatings etc. Equal amounts shall mean from about 40% to about 15% of each w/w. In a particular embodiment, this is from about 30% to about 20% w/w of each and more particularly about 25% of each w/w.

An additional aspect of the invention provides a method of delivering a dietary supplement that promotes darkening of human hair color upon periodic oral consumption of the dietary supplement.

This invention generally relates to a dietary supplement which is useful for the promotion of pigment restoration in human subjects. The dietary supplement of the present invention supplies useful nutrients for hair growth, development, and pigmentation. In particular, this invention relates to a composition which, as to human hair, (i) delays going grey maintains natural color, and/or (ii) has new growth including a higher amount of the original youthful pigmentation or the new growth having the original pigmentation in its entirety that would not otherwise be present. This effect is collectively referred to as "pigment augmentation". The periodic usage of the present dietary supplement provides pigment augmentation.

This invention generally relates to a dietary supplement which is useful for the promotion of pigment augmentation in human subjects. Individuals who have not turned grey or have just begun the graying process may be able, in some instances, to maintain, and perhaps even enhance, their natural hair color without the use of dyes, colorants, or the like. The dietary supplement of the present invention contains, in effective dosage or amounts, black beans, black seeds, walnuts and flaxseeds. The dietary supplement of this invention is adapted to be administered on a regular basis for hair pigment augmentation.

One object of the present invention is to provide a dietary supplement for promoting pigment augmentation, the dietary supplement comprising, in effective dosage, black beans, black seeds, walnuts and flaxseeds (the ingredients are arranged in substantially equal amounts, approximately of 25 percent each in the weight, excluding ancillary dosage form elements), wherein the dietary supplement, when administered to a human on a regular basis, is effective in hair pigment augmentation.

DETAILED DESCRIPTION OF THE INVENTION

One aspect of the invention provides a mixture, combination, a powder of natural ingredients. The ingredients are arranged in substantially equal amounts, approximately 25 percent each in total mixture. The main ingredients of the composition are as follows: black beans, black seeds, walnuts and flaxseeds. The description of the main ingredients is provided herein below.

Ingredient 1

Black Turtle Bean (i.e. *frijol negro*) or *Phaseolus vulgaris* is reported to have nutritional benefits and is known for its Antioxidant properties. Oxidation is a chemical reaction that transfers electrons from a substance to an oxidizing agent. Oxidation reactions can produce free radicals, which start chain reactions that damage cells. Antioxidants terminate these chain reactions by removing free radical intermediates, and inhibit other oxidation reactions by being oxidized themselves Ingredient 2

Black Seed (i.e. *Nigella sativa*) also known as black cumin, is a well-known herb, and its seeds are widely available for use as a spice or condiment. The present invention relates to the dietary supplement which includes black seeds in combination with other ingredients.

Ingredient 3

Walnuts, are also referred to either as *Juglans Regia* or *Juglans Nigra*, are also known as the Black Walnut or White Walnut. The present invention is directed to the dietary supplement which comprises among other ingredients walnuts.

Ingredient 4

Flaxseed is also termed as Linseed, *Linum usitatissimum* and Flax. Flaxseed is one of efficient plant source of omega 3 fatty acids. Flaxseed is rich in EFA-Essential fatty acids which are valuable to human body. Without being bound by any particular theory, it is believed that essential fatty acids work throughout the body to protect cell membranes. Alpha-linolenic acid (ALA), an omega 3 fatty acid found in flaxseed can be used in the treatment of various ailments. Flaxseed is particularly rich in lignans, special compounds also found in other seeds, grains and legumes. Flaxseed oil is highly prone to rancidity since light and oxygen can break down the essential fatty acid. The dietary supplement of the invention among other ingredients includes Flaxseed.

A method of producing the dietary supplement of the invention including treatment of each ingredient will be discussed hereinbelow. As to the first ingredient, black turtle beans or frijol negro in the raw form are obtained and boiled for approximately 15 to 45 minutes. Particular note is made to boiling for about 25 minutes. After boiling and dehydration the dissemination step is taking place, so as to disseminate beans to small particles and prepare a black bean powder. One useful method of obtaining the black bean powder is to grind the initially dehydrated black beans.

As to the black seeds or *Nigella sativa* processing, the seeds are initially taken in their raw natural form (no boiling, drying, etc. is required). Seeds may be ground or pulverized to a powder to facilitate dosage form formation.

As to the walnuts component, they are also taken in their natural form and ground to produce a fine powder of this ingredient.

The flaxseed component is also treated in a manner similar to that discussed above. This means that the flaxseed in its raw form is incorporated into a dosage form in a fine powder. In the next and final step of the method, the ingredients are mixed in equal quantities, i.e., in about 25 percent range. In this manner, a powder combining all ingredients of the dietary supplement is obtained.

Powders are well known in the pharmaceutical arts. Generally speaking, powders are termed very coarse with dimensions of about 10,000 microns, while extremely fine powders approach colloidal dimensions of about 1 micron or less. USP employs descriptive terms such as very coarse, moderately coarse, fine and very fine. Give the breadth of the dosage forms presented here and as a matter of convenience, powders will be broadly understood to include granules. Granules typically fall within the range of a No. 4 to a No. 20 sieve size.

The dietary supplement of the invention for promoting healthy hair including hair pigment restoration may be administered orally as a mixture. Convenient dosage forms include capsules, tablets, regular preparations, or liquid preparation. In one embodiment, one tablespoon of the mixture is administered on a daily basis or for a prescribed duration of time.

EXAMPLES

Test No. 1—Subject One (65 year old male, smoker) is administered a mixture containing:

250 mg powdered black bean,
250 mg powdered black seed,
250 mg powdered flax seed, and
250 mg powdered black walnut.

The mixture is administered daily for 24 months. At the beginning of the study, the subject's hair is salt and pepper mixed with about 70% to 80% grey. At the end of 24 months, the hair is about 50% black. No other side effects occurred.

All percentages are determined as follows: prior to dosing, a sample of at least 200 un-dyed hairs is taken at random from the subject's head. The hairs are evaluated as to color (subject's original) or grey/white under 20× magnification in north light. All later samples are taken from the subject's head and the orientation of the hair maintained such that only the portion within 2 cm of the scalp are assessed for color.

Test No. 2—Subject Two (58 year old male, non-smoker, brown hair) is administered a gel capsule containing:
  200 mg powdered black bean;
  300 mg powdered black seed;
  200 mg powdered flaxseed and
  300 mg powdered black walnut.

These were mixed with 50 mg methyl cellulose. One capsule is taken daily for 18 months. At the beginning of the study, the subject's hair is salt and pepper mixed with 90% grey. At the end of 18 months, the subject's hair remains salt and pepper mixed with about 30% grey. Four months after ceasing treatment, the subject's hair remains a salt and pepper mixed with 30% grey.

Test No. 3—Subject Three (20 year old male, non-smoker, black hair) is administered a mixture containing:
  250 mg powdered black bean,
  250 mg powdered black seed,
  250 mg powdered flax seed, and
  250 mg powdered black walnut.

These were mixed with 50 mg methyl cellulose. The mixture is taken daily for 5 months. At the beginning of the study, the subject's hair contains 10% grey. At the end of the 5 months, the hair is 92% black and 8% grey.

Test No. 4—Subject Four (47 year old female, non-smoker, black hair) is administered a mixture containing:
  270 mg powdered black bean,
  270 mg powdered black seed,
  270 mg powdered flax seed, and
  270 mg powdered black walnut.

The mixture is administered daily for 22 months. At the beginning of the study the subject's hair is a salt and pepper mix with 40% to 45% grey. At the end of the 22 months the subject's hair is 80% black and 20% grey. No other side effects are reported.

Test No. 5—Subject Five (57 year old female non-smoker, brown hair) is administered a capsule containing:
  240 mg powdered black bean;
  240 mg powdered black seed;
  240 mg powdered flaxseed and
  240 mg powdered black walnut.

One capsule is administered daily for 26 months. At the beginning of the study subject's hair is 70% grey. At the end of the 26 months, the subject's hair is 85% brown and 15% grey.

In the above Examples, the dosages could be increased or decreased for individual cases. It is generally preferred that the standard dosage be maintained until the desired results are obtained. Thereafter, the standard or even a reduced dosage could be used for maintenance purposes as needed in individual cases.

The formulations of this invention, including the formulation included in these Examples, could be in the form of a tablespoon of the mixture of the ingredients or other forms that may be more acceptable to the consumer. Additionally, the total and/or relative amounts of the various ingredients could be increased or decreased per unit to allow the consumer to take more or fewer dosages per day.

The present invention relates to a dietary supplement that is useful in promoting and maintaining healthy hair and is useful in retarding, preventing, suppressing, and reversing the graying of hair. The dietary supplement of the present invention supplies useful nutrients for hair growth, development, and pigmentation. Thus, in at least some instances for already-turned grey individuals, the natural hair color can be restored, and maintained, naturally without the use of dyes, colorants, or the like. In a similar manner, individuals who have not turned grey or have just begun the graying process may be able, in some instances, to maintain and enhance their natural hair color without the use of dyes, colorants, or the like. The dietary supplement of the present invention contains in effective amounts, black beans, black seeds, walnuts and flaxseeds in one embodiment. In one embodiment, the ingredients are arranged in substantially equal amounts, approximately of 25 percent each in the total mixture weight. Other compositions of the ingredients in the total mixture of dietary supplement are within the scope of the invention. The dietary supplement of this invention is designed to be orally administered on a regular basis (e.g., one to four times daily) for the promotion and maintenance of healthy human hair and hair pigment restoration and maintenance.

In the same embodiment, the dietary supplement is administered orally once daily. Frequency of administration should depend on the dose per unit (a tablespoon of mixture, capsule or tablet) and the desired level of ingestion. Dose levels/unit can be adjusted to provide the recommended levels of ingredients per day in a reasonable number of units (e.g. a tablespoon of mixture, two capsules or tablets taken twice a day).

As discussed above, a typical dose/unit of the dietary supplement of the invention is one tablespoon or other equivalents thereof which is taken on a daily basis. However, the dietary supplement of different quantities or in the form of a capsule or tablet is within the scope of the invention.

Use of the dietary supplement of this invention on a regular basis (e.g., daily) should promote and encourage healthy hair, especially scalp hair. For some individuals, the use of this dietary supplement can retard, prevent, suppress, and even reverse the graying of hair. Thus, at least for some already-turned grey individuals, the natural hair color can be restored, and maintained, naturally without the use of dyes, colorants, or the like. It is estimated that many grey-haired individuals will be able to at least partially restore their natural hair color using the present dietary supplement on a regular basis.

The visible effects of administering the dietary supplement may require new growth of the hair to occur. The regrowth process may take several months to be noticed for a specific individual. Once a more natural hair color has been restored, the dosage of the dietary supplement or the frequency of use can, if desired, be adjusted or reduced while still maintaining the desired effects. Nonetheless, it is generally preferred that daily use at the same dosage levels be continued for maximum benefit.

The ingredients of the dietary supplement are selected and prepared to provide a composition that is effective at causing human scalp and facial hair to darken, and to promote hair growth after a period of repeated usage. Although not wishing to be bound by any theory, it is believed that the composition of natural ingredients, in the form of dietary supplement, described herein in combination with the effective amounts of each ingredient, function to produce a synergistic interaction combined with favorable digestibility and storage stability characteristics, and thus represents a viable treatment of promoting hair pigment restoration.

The compositions of this invention individually or in combination are employed in admixture with conventional excipients, i.e., pharmaceutically acceptable organic or inorganic carrier substances suitable for parenteral, enteral (e.g., oral) application, etc., which do not deleteriously react with the active compositions. Suitable pharmaceutically acceptable carriers include but are not limited to water, salt solutions, vegetable oils, gelatin, etc. The ingredients of the dietary supplement can be sterilized and if desired mixed with auxiliary agents, e.g., preservatives, stabilizers, wetting agents, emulsifiers, flavoring and/or aromatic substances and the like which do not deleteriously react with the active compositions.

Although the dietary/food supplement of the invention has been described with respect to a particular embodiment, it is understood that variations, substitutions, alterations, and modifications of the ingredients may be made by one of skill in the art based on the disclosure contained herein.

What is claimed is:

1. An orally administered hair pigment augmenting dietary supplement in the form of a fine powder consisting of an effective amount of powdered black beans, powdered black seeds, powdered flaxseeds, and powdered black walnut.

2. The hair pigment augmenting dietary supplement of claim 1, wherein the dietary supplement contains approximately 25% of the powdered black beans, approximately 25% of the powdered black seeds, approximately 25% of the powdered flaxseeds, and approximately 25% of the powdered black walnut and wherein the dietary supplement contains equal amounts of powdered black beans, powdered black seeds, powdered flaxseeds and powdered black walnut.

3. The hair pigment augmenting dietary supplement of claim 2, wherein the dietary supplement is administered in an amount of one tablespoon.

4. The hair pigment augmenting dietary supplement of claim 2, wherein the dietary supplement is administered as a mixture, capsules or tablets.

5. An orally administered hair pigment augmenting dietary supplement consisting of a fine powder consisting of:
    from about 200 mg to about 250 mg powdered black beans;
    from about 200 mg to about 250 mg powdered black seeds;
    from about 200 to 250 mg powdered flaxseeds; and
    from about 200 mg to about 250 mg powdered black walnut,
wherein the dietary supplement is administered in a dosage form and wherein the total amount of powdered black beans, powdered black seeds, powdered flaxseeds, and powdered black walnut is about 1000 mg or less.

6. The hair pigment augmenting dietary supplement of claim 5, wherein the total amount of powdered black beans, powdered black seeds, powdered flaxseeds, and powdered black walnut is about 950 mg or less.

7. The hair pigment augmenting dietary supplement of claim 5, wherein the total amount of powdered black beans, powdered black seeds, powdered flaxseeds, and powdered black walnut is about 900 mg or less.

8. The hair pigment augmenting dietary supplement of claim 4, wherein the dietary supplement is administered as a capsule or tablet.

9. The dietary supplement of claim 5, wherein the dosage form is a capsule or tablet.

* * * * *